# United States Patent
Shen et al.

(10) Patent No.: US 10,408,655 B2
(45) Date of Patent: Sep. 10, 2019

(54) TEMPERATURE COMPENSATION OF A SIGNAL IN A VIBRATORY METER

(71) Applicant: Micro Motion, Inc., Boulder, CO (US)

(72) Inventors: Kai Shen, Nanjing (CN); Lingjun Wang, Nanjing (CN); Xin Li, Nanjing (CN); Huan Liu, Nanjing (CN); Richard L Maginnis, Lafayette, CO (US)

(73) Assignee: Micro Motion, Inc., Boulder, CO (US)

( * ) Notice: Subject to any disclaimer, the term of this patent is extended or adjusted under 35 U.S.C. 154(b) by 171 days.

(21) Appl. No.: 15/551,172

(22) PCT Filed: Mar. 13, 2015

(86) PCT No.: PCT/CN2015/074155
§ 371 (c)(1),
(2) Date: Aug. 15, 2017

(87) PCT Pub. No.: WO2016/145557
PCT Pub. Date: Sep. 22, 2016

(65) Prior Publication Data
US 2018/0031404 A1     Feb. 1, 2018

(51) Int. Cl.
*G01F 15/02*     (2006.01)
*G01F 1/84*      (2006.01)
*G01F 25/00*     (2006.01)
*G01N 9/00*      (2006.01)

(52) U.S. Cl.
CPC .......... *G01F 15/022* (2013.01); *G01F 1/8431* (2013.01); *G01F 1/8468* (2013.01); *G01F 1/8436* (2013.01); *G01F 15/024* (2013.01); *G01F 25/0007* (2013.01); *G01N 2009/006* (2013.01)

(58) Field of Classification Search
CPC ...... G01F 15/02; G01F 15/022; G01F 1/8431; G01F 1/8468
See application file for complete search history.

(56) References Cited

U.S. PATENT DOCUMENTS

| | | | | |
|---|---|---|---|---|
| 4,911,006 A | * | 3/1990 | Hargarten | ................ B67D 7/08 |
| | | | | 702/183 |
| 6,125,706 A | * | 10/2000 | Buttram | ................. B06B 1/045 |
| | | | | 73/643 |
| 6,311,136 B1 | * | 10/2001 | Henry | .................. G01F 1/8404 |
| | | | | 702/45 |

(Continued)

FOREIGN PATENT DOCUMENTS

| | | |
|---|---|---|
| DE | 10257322 A1 | 6/2004 |
| WO | 2008039203 A1 | 4/2008 |

(Continued)

*Primary Examiner* — Peter J Macchiarolo
*Assistant Examiner* — Nathaniel J Kolb
(74) *Attorney, Agent, or Firm* — The Ollila Law Group LLC (57) ABSTRACT

A method for temperature compensation of a signal in a vibratory meter is provided. The method includes obtaining one or more signals from a meter assembly in the vibratory meter, providing the one or more signals to a meter electronics of the vibratory meter, and compensating the one or more signals with a signal parameter offset, wherein the signal parameter offset is based on a temperature of the meter electronics.

20 Claims, 6 Drawing Sheets

(56) References Cited

U.S. PATENT DOCUMENTS

| | | | |
|---|---|---|---|
| 6,618,684 B1 * | 9/2003 | Beroset | G01R 11/185 702/99 |
| 2011/0072912 A1 | 3/2011 | Loving | |
| 2012/0125123 A1 * | 5/2012 | Hays | G01F 1/8431 73/861.357 |
| 2012/0125124 A1 * | 5/2012 | Hays | G01F 1/8436 73/861.357 |
| 2014/0100808 A1 | 4/2014 | Komati et al. | |

FOREIGN PATENT DOCUMENTS

| | | |
|---|---|---|
| WO | 2011019344 A2 | 2/2011 |
| WO | 2014172111 A1 | 10/2014 |

\* cited by examiner

TEMPERATURE COMPENSATION OF A SIGNAL IN A VIBRATORY METER

TECHNICAL FIELD

The embodiments described below relate to temperature compensation of a signal from a vibrating structure and, more particularly, to temperature compensation of a signal in a vibratory meter.

BACKGROUND

Sensors are often used to measure a motion of an object. For example, vibratory meters typically use sensors to measure the position, velocity, or acceleration of a tube. In particular, the vibratory meter can use a driver to vibrate the tube filled with material such as a fluid. The sensors can measure a movement of the tube to determine properties of the fluid in the tube. For example, a sensor can be coupled to the tube filled with material proximate a first fluid port and a second sensor can be coupled to the tube filled with material proximate a second fluid port. The time delay between the first and second sensor can be proportional to the flow rate of the material. The time delay can be determined from two signals provided by the first and second sensors. The two signals are typically analog signals.

Electronics in the vibratory meter can condition the analog signals with operations such as filtering, amplification, or the like, so the analog signals can be digitized. The electronics that condition the analog signals may be sensitive to the temperature changes. For example, the cutoff frequency of a low-pass filter can increase due to increases in temperature of an operational amplifier in the low-pass filter. Other electronic components, such as, for example, diodes, capacitors, inductors, and resistors can also cause output variations that are due to temperature changes in and around the electronics.

The vibratory meter is typically installed in environments with a wide range of temperature specifications. For example, the vibratory meter may be installed on an oil platform where the ambient temperature can be about −40° C. and then later moved to a different oil platform where the temperature can be over 50° C. In addition, the temperatures around the electronics can vary due to electrical current heating the electronic components. Other sources of uncontrollable temperature changes may also be present, such as extremely low fluid temperatures in cryogenic applications. As a result, the signals from the sensors can change due to temperature variation while being conditioned by the electronics.

Accordingly, there is a need for temperature compensation of a signal in a vibratory meter. There is also a need for temperature compensation of the signal affected by temperature variations in and around the meter electronics of the vibratory meter.

SUMMARY

A method for temperature compensation of a signal in a vibratory meter is provided. According to an embodiment, the method comprises obtaining one or more signals from a meter assembly in the vibratory meter, providing the one or more signals to a meter electronics of the vibratory meter, and compensating the one or more signals with a signal parameter offset, wherein the signal parameter offset is based on a temperature of the meter electronics.

A method for temperature compensation of a signal in a vibratory meter is provided. According to an embodiment, the method comprises obtaining one or more signals from a meter assembly in the vibratory meter, providing the one or more signals to a meter electronics of the vibratory meter, measuring a temperature of the meter electronics, and generating a signal parameter offset based on the measured temperature.

An apparatus for temperature compensation of a signal in a vibratory meter is provided. According to an embodiment, the apparatus comprises a meter assembly in a vibratory meter, the meter assembly being configured to provide one or more signals, a meter electronics communicatively coupled to the meter assembly, the meter electronics being configured to receive the one or more signals from the meter assembly, and a temperature sensor in communication with the meter electronics, the temperature sensor being configured to measure a temperature of the meter electronics and provide the temperature measurement to the meter electronics. The meter electronics is configured to provide a signal parameter offset based on the temperature measurement and compensate the one or more signals with the signal parameter offset.

Aspects

According to an aspect, a method for temperature compensation of a signal in a vibratory meter comprises obtaining one or more signals from a meter assembly in the vibratory meter, providing the one or more signals to a meter electronics of the vibratory meter, and compensating the one or more signals with a signal parameter offset, wherein the signal parameter offset is based on a temperature of the meter electronics.

Preferably, the step of obtaining the one or more signals from the meter assembly comprises obtaining one or more signals from at least one sensor attached to a tube in the meter assembly.

Preferably, the one or more signals includes a signal that is previously zeroed at a nominal temperature.

Preferably, the method further comprises at least one of determining a time delay between two of the one or more signals and compensating the time delay with the signal parameter offset, determining a frequency of the one or more signals and compensating the frequency with the signal parameter offset, and determining an amplitude of the one or more signals and compensating the amplitude with the signal parameter offset.

Preferably, the method further comprises measuring the temperature of the meter electronics and comparing the measured temperature with a stored measured temperature.

Preferably, the method further comprises measuring the temperature of the meter electronics and correlating the measured temperature with the signal parameter offset.

Preferably, the one or more signals is comprised of at least one digital signal.

Preferably, the signal parameter offset is a digital value that is added to at least one of the one or more signals.

Preferably, the temperature of the meter electronics is comprised of a temperature of an analog circuit in the meter electronics.

According to an aspect, a method for temperature compensation of a signal in a vibratory meter comprises obtaining one or more signals from a meter assembly in the vibratory meter, providing the one or more signals to a meter electronics of the vibratory meter, measuring a temperature of the meter electronics, and generating a signal parameter offset based on the measured temperature.

Preferably, the step of generating the signal parameter offset based on the measured temperature comprises determining the difference between a nominal temperature value and a value determined from the one or more signals.

Preferably, the method further comprises varying the temperature of the meter electronics by varying the temperature of the ambient environment.

Preferably, the method further comprises storing the signal parameter offset and the temperature measurement in the meter electronics.

Preferably, the method further comprises storing a correlation between the temperature measurement and the signal parameter offset in the meter electronics.

According to an aspect, an apparatus (300) for temperature compensation of a signal in a vibratory meter (5) comprises a meter assembly (10) in a vibratory meter (5), the meter assembly (10) being configured to provide one or more signals, a meter electronics (20) communicatively coupled to the meter assembly (10), the meter electronics (20) being configured to receive the one or more signals from the meter assembly (10), and a temperature sensor (390) in communication with the meter electronics (20), the temperature sensor (390) being configured to measure a temperature of the meter electronics (20) and provide the temperature measurement (392) to the meter electronics (20). The meter electronics (20) is configured to provide a signal parameter offset based on the temperature measurement (392) and compensate the one or more signals with the signal parameter offset.

Preferably, the meter assembly (10) is comprised of at least one flow tube (130, 130') and at least one pick-off sensor (170*l*, 170*r*, 310, 320) coupled to the at least one flow tube (130, 130').

Preferably, the meter electronics (20) is further configured to zero the one or more signals prior to compensating the one or more signals with the signal parameter offset.

Preferably, the meter electronics (20) is further configured to at least one of determine a time delay between two of the one or more signals and compensate the time delay with the signal parameter offset, determine a frequency of the one or more signals and compensate the frequency with the signal parameter offset, and determine an amplitude of the one or more signals and compensate the amplitude with the signal parameter offset.

Preferably, the meter electronics (20) provides the signal parameter offset by comparing the temperature measurement (392) to a stored temperature measurement (224) correlated with the stored signal parameter offset (225).

Preferably, the meter electronics (20) is further configured to store the temperature measurement (224) in a storage system (220) in the meter electronics (20).

Preferably, the temperature sensor (390) is further configured to measure the temperature of an analog circuit (330) that receives the one or more signals from the meter assembly (10).

BRIEF DESCRIPTION OF THE DRAWINGS

The same reference number represents the same element on all drawings. It should be understood that the drawings are not necessarily to scale.

DETAILED DESCRIPTION

FIGS. 1-6 and the following description depict specific examples to teach those skilled in the art how to make and use the best mode of embodiments of a temperature compensation of a signal in a vibratory meter. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the temperature compensation of the signal in the vibratory meter. As a result, the embodiments described below are not limited to the specific examples described below, but only by the claims and their equivalents.

Figure 1:
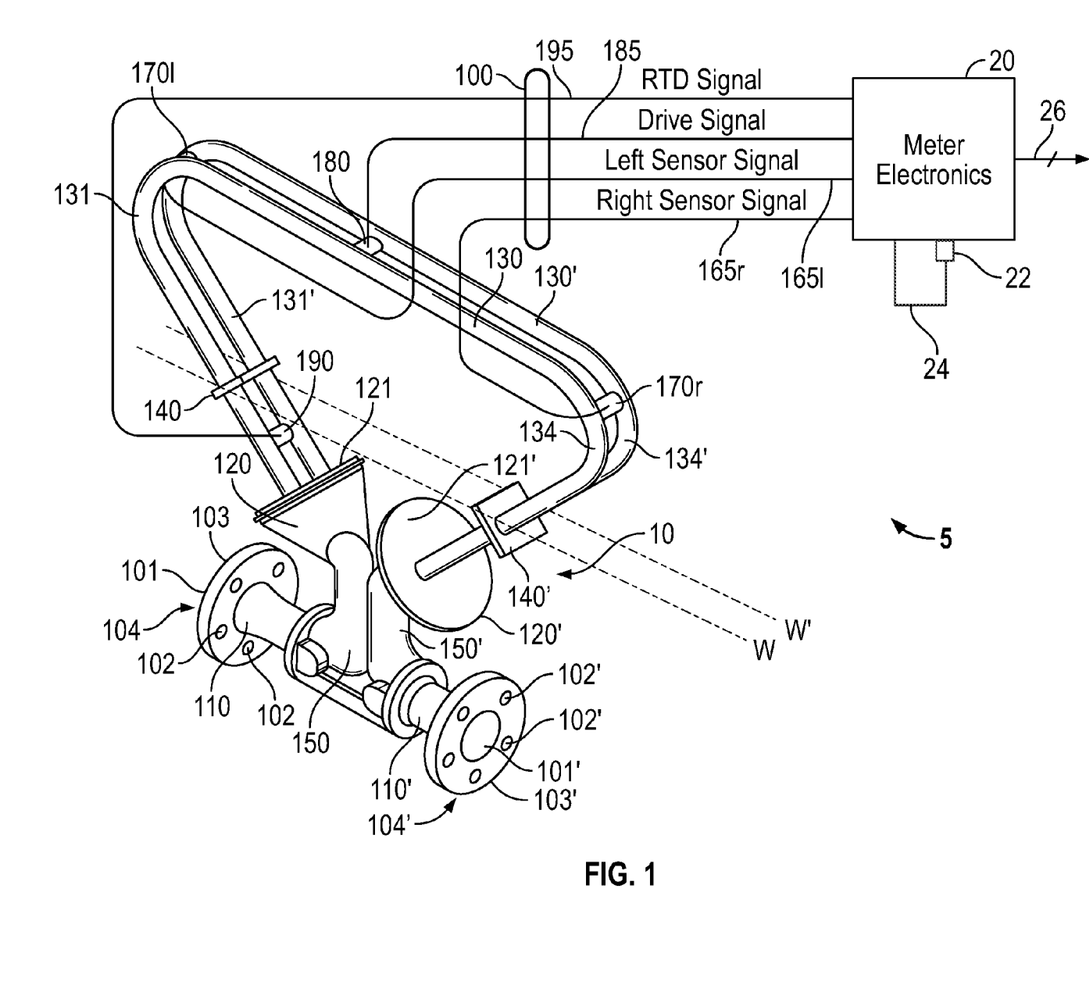
FIG. 1 shows a vibratory meter 5 comprising a meter assembly 10 and meter electronics 20.

FIG. 1 shows a vibratory meter 5 comprising a meter assembly 10 and meter electronics 20. The meter assembly 10 responds to mass flow rate and density of a process material. The meter electronics 20 is connected to the meter assembly 10 via leads 100 to provide density, mass flow rate, and temperature information over path 26, as well as other information. A Coriolis flow meter structure is described although it is apparent to those skilled in the art that the present invention could be practiced as a vibrating tube densitometer, tuning fork densitometer, or the like.

The meter assembly 10 includes a pair of manifolds 150 and 150', flanges 103 and 103' having flange necks 110 and 110', a pair of parallel flow tubes 130 and 130', drive mechanism 180, resistive temperature detector (RTD) 190, and a pair of pick-off sensors 170*l* and 170*r*. Flow tubes 130 and 130' have two essentially straight inlet legs 131, 131' and outlet legs 134, 134', which converge towards each other at flow tube mounting blocks 120 and 120'. The flow tubes 130, 130' bend at two symmetrical locations along their length and are essentially parallel throughout their length. Brace bars 140 and 140' serve to define the axis W and W' about which each flow tube 130, 130' oscillates.

The side legs 131, 131' and 134, 134' of the flow tubes 130, 130' are fixedly attached to flow tube mounting blocks 120 and 120' and these blocks, in turn, are fixedly attached to manifolds 150 and 150'. This provides a continuous closed material path through meter assembly 10.

When flanges 103 and 103', having holes 102 and 102' are connected, via inlet end 104 and outlet end 104' into a process line (not shown) which carries the process material that is being measured, material enters inlet end 104 of the meter through an orifice 101 in the flange 103 and is conducted through the manifold 150 to the flow tube mounting block 120 having a surface 121. Within the manifold 150 the material is divided and routed through the flow tubes 130, 130'. Upon exiting the flow tubes 130, 130', the process material is recombined in a single stream within the block 120' having a surface 121' and the manifold 150' and is thereafter routed to outlet end 104' connected by the flange 103' having holes 102' to the process line (not shown).

The flow tubes 130, 130' are selected and appropriately mounted to the flow tube mounting blocks 120, 120' so as to have substantially the same mass distribution, moments of inertia and Young's modulus about bending axes W-W and W'-W', respectively. These bending axes go through the brace bars 140, 140'. Inasmuch as the Young's modulus of the flow tubes change with temperature, and this change affects the calculation of flow and density, RTD 190 is mounted to flow tube 130' to continuously measure the temperature of the flow tube 130'. The temperature of the flow tube 130' and hence the voltage appearing across the RTD 190 for a given current passing therethrough is governed by the temperature of the material passing through the flow tube 130'. The temperature dependent voltage appearing across the RTD 190 is used in a well-known method by the meter electronics 20 to compensate for the change in elastic modulus of the flow tubes 130, 130' due to any changes in flow tube temperature. The RTD 190 is connected to the meter electronics 20 by lead 195.

Both of the flow tubes 130, 130' are driven by drive mechanism 180 in opposite directions about their respective bending axes W and W' and at what is termed the first out-of-phase bending mode of the flow meter. This drive mechanism 180 may comprise any one of many well-known arrangements, such as a magnet mounted to the flow tube 130' and an opposing coil mounted to the flow tube 130 and through which an alternating current is passed for vibrating both flow tubes 130, 130'. A suitable drive signal is applied by the meter electronics 20, via lead 185, to the drive mechanism 180.

The meter electronics 20 receives the RTD temperature signal on lead 195, and the left and right sensor signals appearing on leads 165*l*, 165*r*, respectively. The meter electronics 20 produces the drive signal appearing on lead 185 to drive mechanism 180 and vibrate tubes 130, 130'. The meter electronics 20 processes the left and right sensor signals and the RTD signal to compute the mass flow rate and the density of the material passing through meter assembly 10. Processing the left and right sensor signals and the RTD signal may include determining the time delay or phase difference between the left and right sensor signal. The processing may also include determining other signal parameters such as the frequency and amplitude of the left and right sensor signals. These and other information, is applied by meter electronics 20 over path 26.

Figure 2:
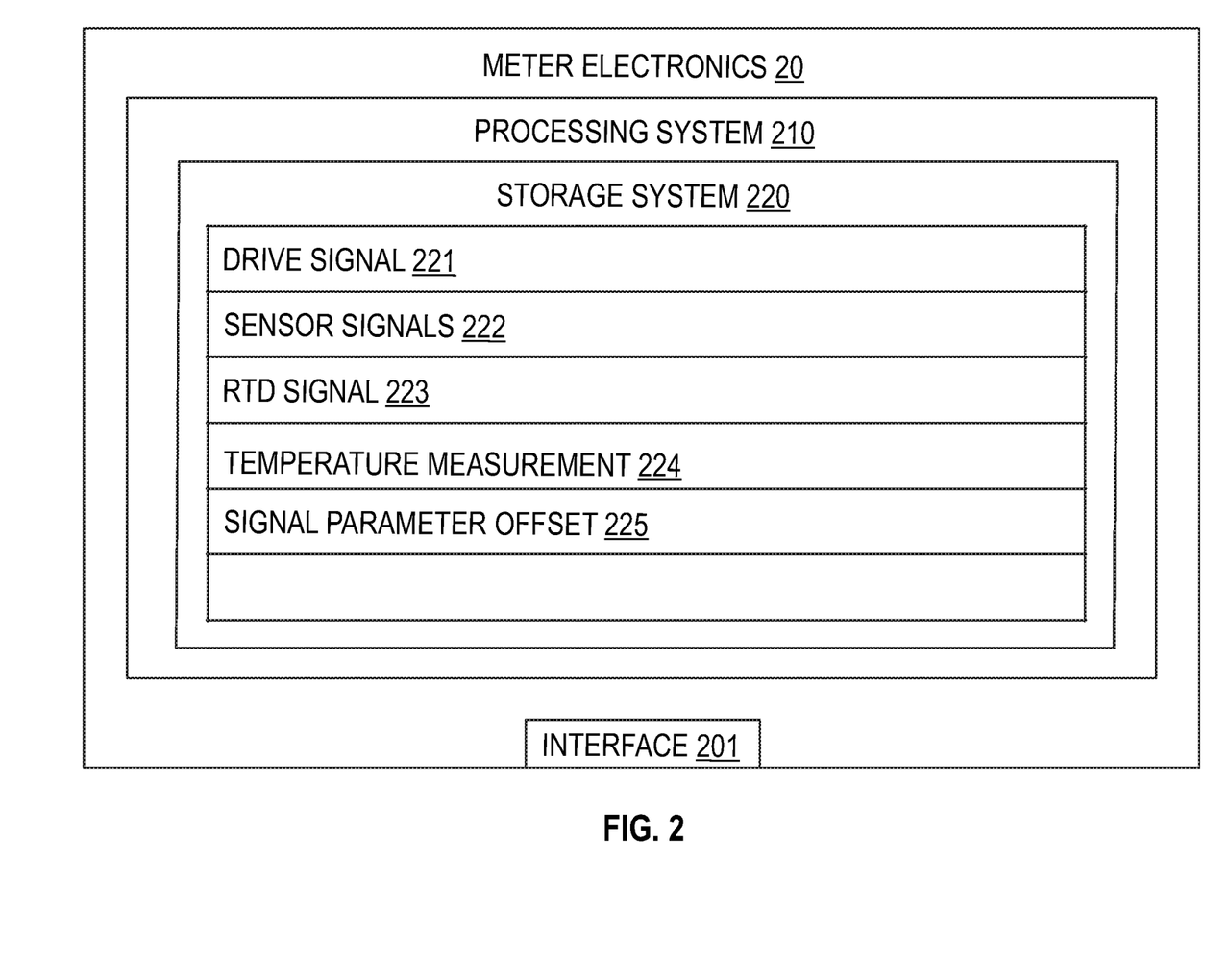
FIG. 2 shows the meter electronics 20 according to an embodiment of the invention.

FIG. 2 shows the meter electronics 20 according to an embodiment of the invention. The meter electronics 20 can include an interface 201 and a processing system 210. The processing system 210 may include a storage system 220. The storage system 220 may comprise an internal memory as shown, or alternatively, may comprise an external memory.

The interface 201 can receive the sensor signals from the drive mechanism 180 and pick-off sensors 170*l*, 170*r* via leads 165*r*, 165*l*, 185. The interface 201 may perform any necessary or desired signal conditioning, such as any manner of formatting, amplification, buffering, etc. Alternatively, some or all of the signal conditioning can be performed in the processing system 210. In addition, the interface 201 can enable communications between the meter electronics 20 and external devices. The interface 201 can be capable of any manner of electronic, optical, or wireless communication.

The interface 201, in an embodiment, may include a digitizer, wherein the sensor signal comprises an analog signal. The digitizer can sample and digitize the analog signal and produce a digital signal. The digitizer can also perform any needed decimation, wherein the digital signal is decimated in order to reduce the amount of signal processing needed and to reduce the processing time.

The processing system 210 can comprise a general purpose computer, a micro-processing system, a logic circuit, or some other general purpose or customized processing device. The processing system 210 can be distributed among multiple processing devices. The processing system 210 can include any manner of integral or independent electronic storage medium, such as the storage system 220.

It should be understood that the meter electronics 20 may include various other components and functions that are generally known in the art. These additional features are omitted from the description and the figures for the purpose of brevity. Therefore, the present invention should not be limited to the specific embodiments shown and discussed.

The meter electronics 20 can use the stored drive signal 221 to generate and supply the drive signal sent over the lead 185 to the drive mechanism 180. For example, the drive signal described with reference to FIG. 1 could be generated from the stored drive signal 221 with a digital-to-analog converter. In addition, the meter electronics 20 can receive, encode, and store the sensor signals received over the leads 165*l*, 165*r* into the stored sensor signals 222. In some embodiments, the sensor signals 222 can include signals received from the drive mechanism 180. The meter electronics 20 may also receive, encode, and store the RTD signal 195 from the RTD 190 as an RTD signal 223, which is coupled to the flow tubes 130, 130'. The meter electronics 20 can process the sensor signals 222 in order to obtain flow characteristics of the material flowing through the flow tubes 130, 130'.

The meter electronics 20 can also process a temperature measurement 224 of the meter electronics 20. The temperature measurement 224 can be one or more stored values that are based on a temperature of the meter electronics 20. In some embodiments, the temperature measurement 224 is based on a temperature of the interface 201. For example, the temperature measurement 224 may be the temperature of the portion of the interface 201 that receives and conditions the sensor signals received over the leads 165*l*, 165*r* for the digitizer, as described in the foregoing.

The meter electronics 20 can also generate and provide a signal parameter offset 225, which may be added to the sensor signals 222. For example, the meter electronics 20 may use the sensor signals 222 to determine a time delay between the left pick-off sensor 170*l* and the right pick-off sensor 170*r*. As can be appreciated, the time delay may have an error due to temperature variation in the meter electronics 20. The signal parameter offset 225 can be added to the time delay to reduce or eliminate the error in the time delay. These and other methods and apparatuses for temperature compensation of a signal in a vibratory meter are described in more detail in the following.

Figure 3:
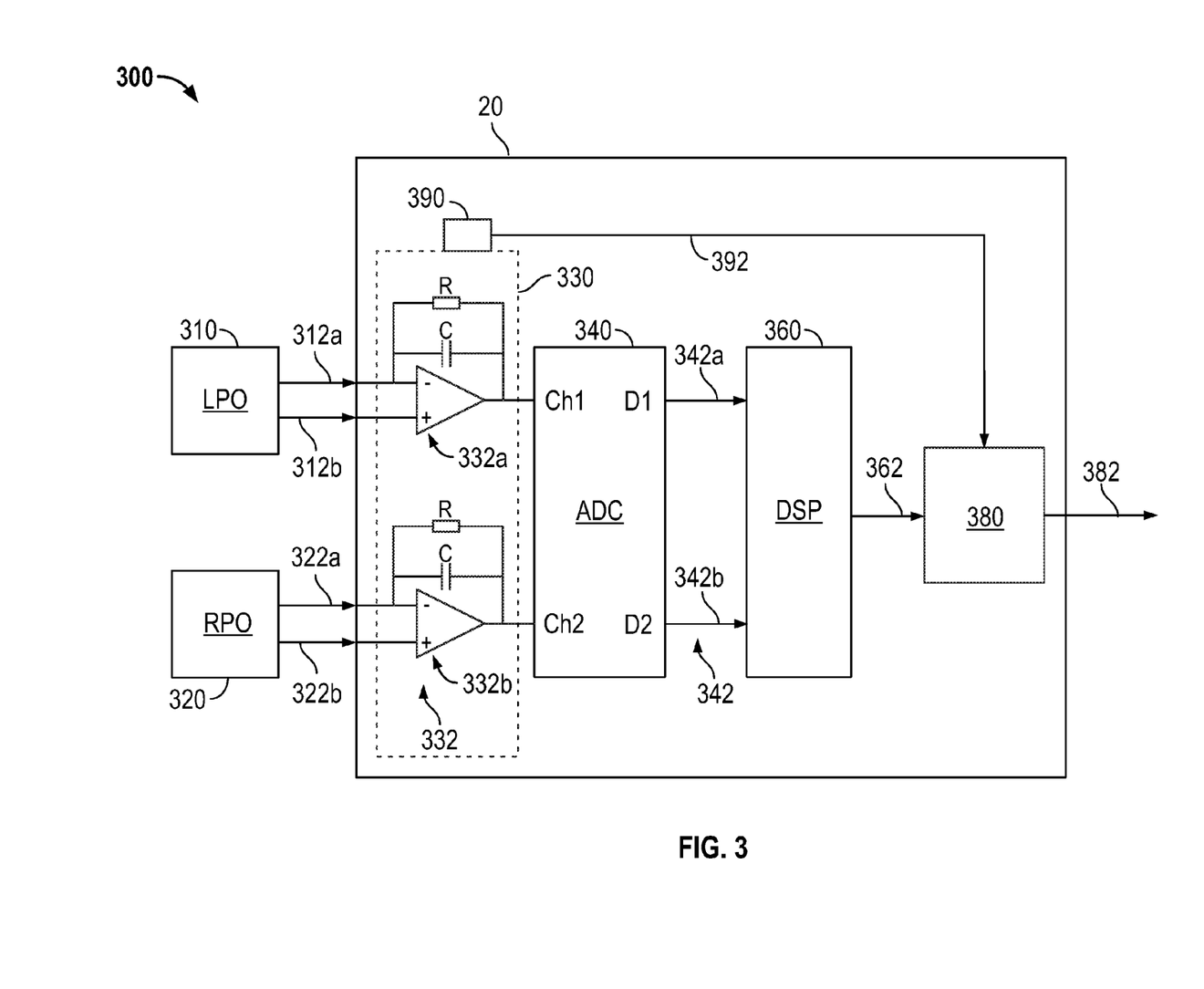
FIG. 3 shows an apparatus 300 for temperature compensation of a signal in a vibratory meter.

FIG. 3 shows an apparatus 300 for temperature compensation of a signal in a vibratory meter. As shown in FIG. 3, the apparatus 300 is represented as a block diagram. The apparatus 300 includes a left pick-off (LPO) sensor 310 and a right pick-off (RPO) sensor 320. The LPO sensor 310 is shown as providing a first LPO signal 312*a* and a second LPO signal 312*b*. The RPO sensor 320 is shown as providing a first RPO signal 322*a* and a second RPO signal 322*b*. The signals 312*a*, 312*b*, 322*a*, 322*b* are provided to an analog circuit 330. The analog circuit 330 is communicatively coupled to an analog-to-digital converter (ADC) 340. The ADC 340 is communicatively coupled to a digital signal processor (DSP) 360 with two digital signals 342. The DSP 360 is communicatively coupled with a DSP output 362 to a processing system 380. The processing system 380 is also shown as being communicatively coupled to a temperature sensor 390 that is disposed proximate to the analog circuit 330.

The pick-off sensors 310, 320 can be any sensor that measures a motion of, for example, the flow tubes 130, 130' described with reference to FIG. 1. Although the apparatus 300 is shown as only including the LPO and RPO sensors 310, 320, other sensors can be employed in alternative embodiments. For example, the RTD signal described with reference to FIG. 1 can also be employed by the apparatus 300. In the embodiment shown, the pick-off sensors 310, 320 are sensors that measure the velocity of the flow tubes 130, 130'. Since the pick-off sensors 310, 320 measure the velocities of two flow tubes 130, 130', two signals are provided from each of the pick-off sensors 310, 320. In the embodiment shown, the LPO signals 312a, 312b may be about 180 degrees out of phase with each other due to the flow tubes 130, 130' being deflected in an out of phase bending mode, although other modes, such as twist and in-phase modes, may be present. Similarly, the RPO signals 322a, 322b may also be about 180 degrees out of phase with each other due to the flow tubes 130, 130' being deflected in the out of phase bending mode. The signals 312a, 312b, 322a, 322b are provided to the analog circuit 330.

The analog circuit 330 can condition the signals 312a, 312b, 322a, 322b for digitization by the ADC 340. In alternative embodiments, the analog circuit 330 can condition other signals, such as the RTD signal described with reference to FIG. 1. In the embodiment shown in FIG. 3, the LPO signals 312a, 312b are provided to a first operational amplifier 332a. The RPO signals 322a, 322b are provided to a second operational amplifier 332b. Although the analog circuit 330 is shown as including the two operational amplifiers 332, more or fewer operational amplifiers, including no operational amplifiers, may be employed in alternative embodiments. Operational amplifiers in the alternative embodiments may include different components such as a different configuration of passive components, or other electronics. For example, a capacitor may be between a voltage supply terminal on the first operational amplifier 332a and a ground. Components other than the operational amplifiers 332 can also be employed in the analog circuit 330, such as transformers, inductors, etc. Additionally or alternatively, the analog circuit 330 can include digital components, such as a multiplexer, along with the analog components.

In the embodiment shown, the operational amplifiers 332 are in a low-pass filter configuration. The cut-off frequency, phase shift, and other electrical properties of the low-pass filter configuration depend on the values of the resistors R and capacitors C. The operational amplifiers 332 are typically designed such that the values of the resistors R and capacitors C are the same in each of the operational amplifiers 332. However, due to tolerance specifications of the resistors R and capacitors C, actual nominal values of the resistors R and capacitors C can deviate from the design nominal values. In addition, actual values of the resistors R and the capacitors C can also drift from the actual nominal values due to variation in the temperature of the meter electronics 20.

For example, in an embodiment, the design nominal value of the capacitors C may be 100 pF. The actual nominal values might be 95 pF for the capacitor C in the first operational amplifier 332a and 105 pF in the second operational amplifier 332b. The capacitors C might be at the actual nominal values when they are, for example, at room temperature. However, the temperature of the analog circuit 330 can vary during operation of the vibratory meter 5 such that the values of the capacitors C drift from the actual nominal values. As a result, the cut-off frequency, phase shift, and other electrical properties of the operational amplifiers 332 can deviate due to temperature changes in the meter electronics 20. The deviation in the electrical properties can cause the signals received by the ADC 340 to change due to temperature variations in the meter electronics 20.

The ADC 340 digitizes the signals provided by the operational amplifiers 332. During digitization, the ADC 340 may sample the signals 312a, 312b, 322a, 322b using a reference voltage. The reference voltage may also deviate due to variations in the temperature of the meter electronics 20. As a result, the digital versions of the signals 312a, 312b, 322a, 322b can also change due to temperature variations in the ADC 340. In the embodiment shown, the ADC 340 is a two channel ADC although more or fewer channels may be employed in alternative embodiments. Additionally or alternatively, the ADCs in the alternative embodiments can be comprised or more or fewer ADCs. For example, two single channel ADCs may be employed in alternative embodiments. Alternatively, a three or more channel ADC can be employed where two of the channels are employed. As shown in FIG. 3, the ADC 340 provides digital signals 342 to the DSP 360.

The digital signals 342 are comprised of a first digital signal 342a and a second digital signal 342b. The first and second digital signal 342a, 342b respectively correspond to the signals provided by the first and second operational amplifier 332a, 332b. Accordingly, the digital signals 342 can be a sequence of digital values that represent the corresponding signals provided by the operational amplifiers 332. As a result, the digital signals 342 also include the variations caused by temperature variations in the meter electronics 20. The digital signals 342 are provided to and processed by the DSP 360 to, for example, determine properties of the fluid in the tubes 130, 130'.

The DSP 360 can perform a variety of signal processing functions such as filtering, decimation, delaying, etc. In the embodiment shown, the DSP 360 can, for example, process the first digital signal 342a and the second digital signal 342b to determine a time delay. The time delay can be proportional to a mass flow rate of fluid in the flow tubes 130, 130'. However, in alternative embodiments, the DSP 360 can perform other operations that correspond to other properties such as the density of the fluid in the flow tubes 130, 130', etc. For example, in an alternative embodiment, a frequency of digital signals can be correlated with the density of material being measured by a tuning fork densitometer. In the embodiment shown, the time delay, or other properties, can be provided to the processing system 380 as the DSP output 362.

The processing system 380 can perform a temperature compensation on the DSP output 362. For example, the processing system 380 can have a stored signal parameter offset that is correlated with a previously measured temperature of the meter electronics 20. The signal parameter offset can be a delay that is, for example, added to the time delay received from the DSP 360 via the DSP output 362. Although a single DSP output 362 is shown, more DSP outputs can be employed in alternative embodiments. Additionally or alternatively, alternative DSP outputs can carry information related to properties other than a time delay or a mass flow rate. In the embodiment shown, as well as other embodiments, the processing system 380 also receives a temperature measurement 392 from the temperature sensor 390 that is proximate the analog circuit 330.

In the embodiment shown, the temperature sensor 390 is part of the meter electronics 20 and is physically proximate to the analog circuit 330. Accordingly, the temperature sensor 390 can measure a temperature of the meter electronics 20. The temperature sensor 390 can convert a temperature of, for example, the analog circuit 330 into a voltage signal. In alternative embodiments, the temperature sensor 390 may not be physically coupled to the meter electronics 20. For example, the temperature sensor 390 can be an infrared sensor that measures the infrared emissions from, for example, the operational amplifiers 332. In these and other embodiments, the measured temperature of the meter electronics 20 can be the temperature of the operational amplifiers 332. The temperature of the operational amplifiers 332 can include, for example, the temperature of the resistors R and capacitors C shown in FIG. 3. Other configurations of the temperature sensor 390 may be employed.

For example, although a single temperature sensor 390 is shown in FIG. 3, more temperature sensors may be included in alternative embodiments. For example, a temperature sensor can be proximate each of the operational amplifiers 332. Accordingly, the temperature of each of the operational amplifiers 332 can be determined, thereby providing two temperature signals that can be processed to determine the correlated signal parameter offset with a desired level of accuracy. In other embodiments, other temperature sensors can be employed to provide additional temperature measurements, which can be employed to provide a signal parameter offset.

Referring to the embodiment shown in FIG. 2, the processing system 380 can correlate the temperature measurement 392 with the stored signal parameter offset 225. For example, the processing system 380 can compare the temperature measurement 392 with a stored temperature measurement 224 that is correlated with the stored signal parameter offset 225. During the comparison, the processing system 380 may determine if the stored temperature measurement 224 is the same as the temperature measurement 392. If the stored temperature measurement 224 and the temperature measurement 392 are the same, then the processing system 380 can select the stored signal parameter offset 225 that is correlated with the stored temperature measurement 224. The process of comparing the temperature measurement 392 with the stored temperature measurement 224 can be performed iteratively until the comparison indicates that the stored temperature measurement 224 is the same as the temperature measurement 392.

Although the comparison between the stored temperature measurement 224 and the temperature measurement 392 is described in the foregoing as based on the comparison indicating that the values are the same, the comparison can also correlate the stored signal parameter offset 225 if the stored temperature measurement 224 and the temperature measurement 392 are not the same. For example, the processing system 380 can compare the temperature measurement 392 with the stored temperature measurement 224 and select the correlated signal parameter offset 225 if the temperature measurement 392 is within a range of values around the stored temperature measurement 224. Other comparison methods may be employed.

As the foregoing illustrates, the signal parameter offset 225 can be based on the temperature of the meter electronics 20. As will be described in more detail in the following, the signal parameter offset 225 can be used to compensate the signals provided to the meter electronics 20.

Compensating a Signal with a Signal Parameter Offset

Figure 4:
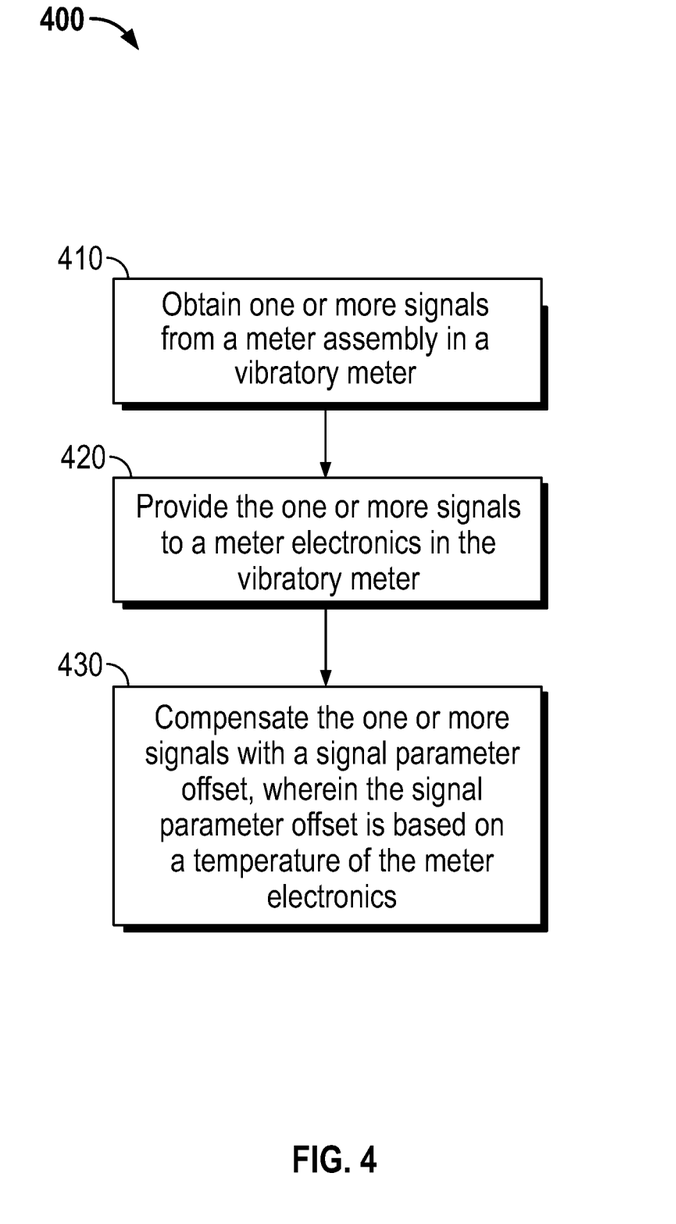
FIG. 4 shows a method 400 for temperature compensation of a signal in a vibratory meter.

FIG. 4 shows a method 400 for temperature compensation of a signal in a vibratory meter. The method 400 can be performed by the meter electronics 20 or other electronics. For example, the method 400 can be performed by the processing system 380 described with reference to FIG. 3. The method 400 begins by obtaining one or more signals from a meter assembly, such as the meter assembly 10 described with reference to FIG. 1, in the vibratory meter in step 410. In step 420, the method 400 provides the one or more signals to a meter electronics, such as the meter electronics 20 described with reference to FIGS. 1-3, in the vibratory meter. The method 400 compensates the one or more signals with a signal parameter offset in step 430. The signal parameter offset is based on a temperature of the meter electronics 20.

In step 410, the method 400 can obtain the one or more signals from the meter assembly in the vibratory meter by measuring, for example, a voltage from the pick-off sensors 170l, 170r. The one or more signals can be obtained with the leads 100 described with reference to FIG. 1. The one or more signals can also be obtained with the pick-off sensors 310, 320 described with reference to FIG. 3. For example, the one or more signals can be the signals 312a, 312b, 322a, 322b shown in FIG. 3. In alternative embodiments, the one or more signals can be obtained by other means, such as wireless transmission, through a multiplexer, or the like. Additionally or alternatively, the one or more signals can be obtained from sensors other than the sensors described in the foregoing.

In step 420, the one or more signals is provided to a meter electronics, such as, for example, the meter electronics 20 described with reference to FIGS. 1-3. The one or more signals may be provided to the meter electronics 20 at the interface 201 shown in FIG. 2. With reference to the embodiment shown in FIG. 3, the one or more signals can also be provided to the analog circuit 330. The analog circuit 330 may perform signal conditioning on the one or more signals. For example, the analog circuit 330 can perform operations such as comparison of the LPO signals 312a, 312b and the RPO signals 322a, 322b.

As described in the foregoing with reference to FIG. 3, the temperature variation in the meter electronics 20 can cause the signals 312a, 312b, 322a, 322b to change. For example, temperature variations in the operational amplifiers 332 can cause the nominal values of the resistors R and capacitors C to drift. As a result, the signals provided by the operational amplifiers 332 can have an error. Additionally or alternatively, temperature variations in the ADC 340 can also cause variations in the signals obtained from the operational amplifiers 332. Accordingly, the one or more signals can include variations prior to being compensated by the signal parameter offset.

In step 430, the one or more signals can be compensated with a signal parameter offset. The signal parameter offset is based on the temperature of the meter electronics. The temperature of the meter electronics 20 can be measured by the temperature sensor 390. The temperature of the meter electronics 20 can, for example, be the temperature of the analog circuit 330 described with reference to FIG. 3. In other embodiments, the temperature can be the temperature of the operational amplifiers 332. Using the temperature measurement 392 of the meter electronics 20, the one or more signals can be compensated with the signal parameter offset with various methods. An exemplary method is described in the following with reference to FIG. 5.

Figure 5:
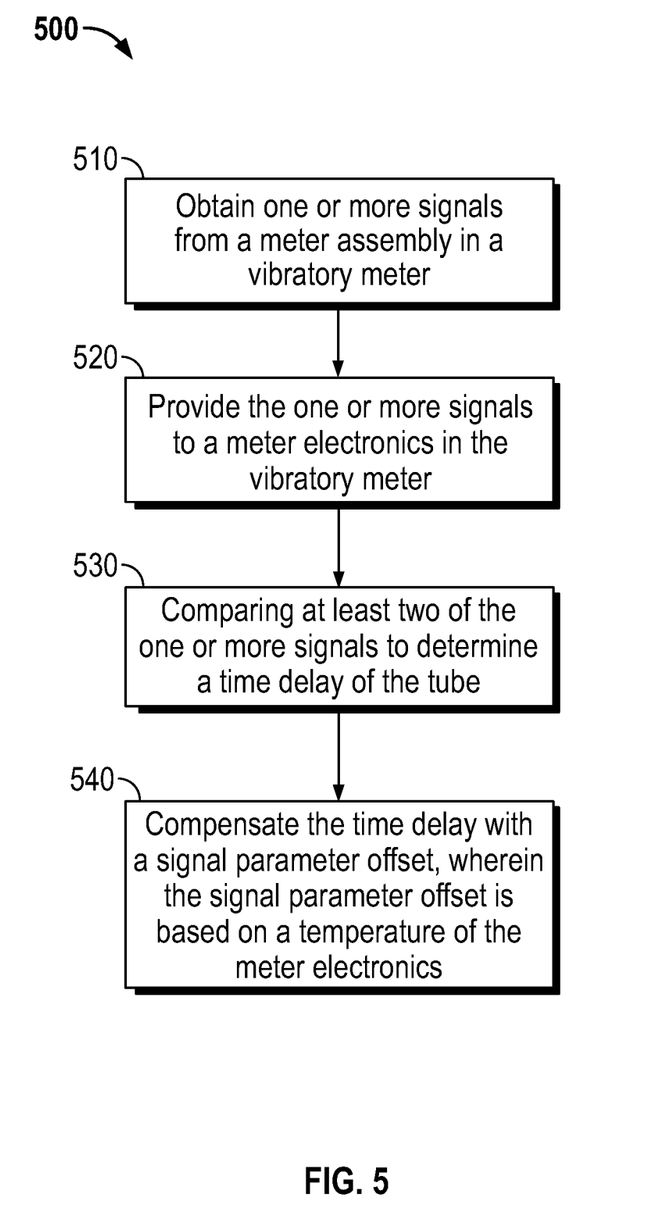
FIG. 5 shows another method 500 for temperature compensation of a signal in a vibratory meter.

FIG. 5 shows another method 500 for temperature compensation of a signal in a vibratory meter. The method 500 begins by obtaining one or more signals from a meter assembly in the vibratory meter in step 510. In step 520, the method 500 provides the one or more signals to a meter electronics of the vibratory meter. The method 500 compares the at least two of the one or more signals to determine a time delay of the tube in step 530. In step 540, the method 500 compensates the time delay with a signal parameter offset. According to the method 500, the signal parameter offset is based on the temperature of the meter electronics.

Similar to the steps 410 and 420 described in the foregoing with reference to FIG. 4, steps 510 and 520 can obtain one or more signals from the meter assembly in the vibratory meter and provide the one or more signals to a meter electronics of the vibratory meter. The steps 510 and 520 can include the embodiments described in the foregoing as well as other embodiments.

In step 530, the time delay is determined from at least two of the one or more signals by, for example, subtracting zero crossing points of the LPO signals 312*a*, 312*b* and the RPO signals 322*a*, 322*b*. The time delay can be determined with various other methods. For example, a phase delay could be determined from the two or more signals and divided by the frequency of one of the one or more signals. The time delay can be determined after the one or more signals are digitized by, for example, the ADC 340. In the embodiment shown in FIG. 3, the time delay can be determined by the DSP 360. Other embodiments can include other processors or electronics that can determine the time delay or other properties.

In step 540, the time delay is compensated with the signal parameter offset by, for example, adding the signal parameter offset to the time delay. As described in the foregoing with reference to FIG. 3, the time delay can vary due to temperature variations in the meter electronics 20. The time delay can be a positive scalar value that is proportional to the flow rate of the fluid in the flow tubes 130, 130' described with reference to FIG. 1. The signal parameter offset can be a negative scalar value that, when added to the time delay, reduces or eliminates the error in the time delay. However, any appropriate representations of the time delay and operations can be employed in these and other embodiments.

The time delay can be compensated in the processing system 380. For example, the processing system 380 can receive the temperature measurement 392 from the temperature sensor 390. As described in the foregoing with reference to FIG. 3, the temperature sensor 390 may compensate the time delay with the signal parameter offset 225. For example, the processing system 380 can compare the temperature measurement 392 with the stored temperature measurement 224 to select the correlated signal parameter offset 225. The selected signal parameter offset 225 can be added to the time delay.

Although the method 500 describes a signal parameter offset 225 that is added to a time delay, the signal parameter offset 225 can be added to other parameters of the signal. For example, the signal parameter offset 225 can be added to a frequency or an amplitude of the signal. In an embodiment, the signal parameter offset 225 can be added to the frequency during a density measurement. The foregoing embodiments illustrate exemplary methods that compensate one or more signals with a signal parameter offset. The following describes how the signal parameter offset may be generated and, in some embodiments, stored in the meter electronics 20.

Generating a Signal Parameter Offset

Figure 6:
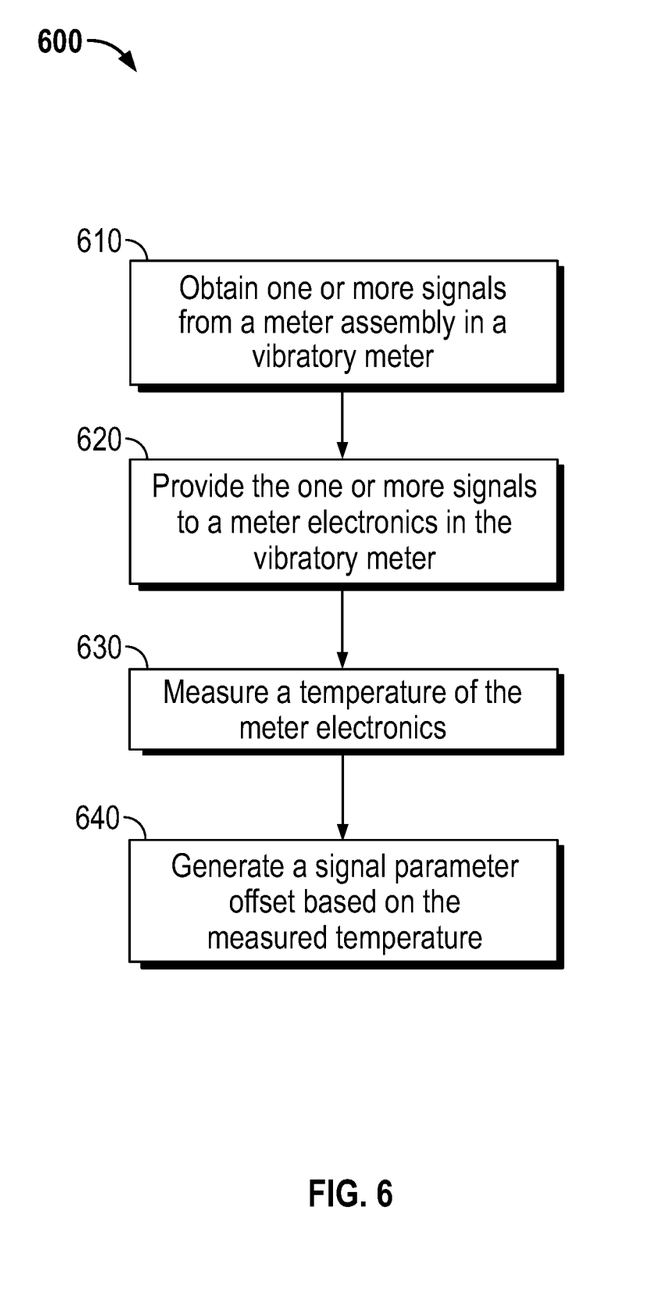
FIG. 6 shows another method 600 for temperature compensation of a signal in a vibratory meter.

FIG. 6 shows another method 600 for temperature compensation of a signal in a vibratory meter. The method 600 begins by obtaining one or more signals from a meter assembly in the vibratory meter in step 610. In step 620, the method 600 provides the one or more signals to a meter electronics of the vibratory meter. The method 600 also measures a temperature of the meter electronics in step 630. In step 640, the method 600 generates a signal parameter offset based on the measured temperature.

Similar to the steps 410 and 420 described in the foregoing with reference to FIG. 4, steps 610 and 620 can obtain one or more signals from the meter assembly in the vibratory meter and provide the one or more signals to a meter electronics of the vibratory meter. The steps 610 and 620 can include the embodiments described in the foregoing as well as other embodiments.

In step 630, the method 600 measures a temperature of the meter electronics. The meter electronics may be the meter electronics 20 described in the foregoing. The temperature of the meter electronics can be measured by the temperature sensor 390 described with reference to FIG. 3 or a different temperature sensor. For example, the temperature of the meter electronics 20 could be measured by a temperature sensor that is not part of the meter electronics 20. Instead, the temperature could be measured by a temperature sensor that is part of testing equipment that calibrates the vibratory meter 5.

For example, the vibratory meter 5, or a portion of the vibratory meter 5, such as the meter electronics 20, could be placed in an environmental test chamber. The environmental test chamber may increase or decrease the temperature of the meter electronics 20 while measuring the temperature with a thermocouple that is affixed to the meter electronics 20. The temperature of the meter electronics 20 can be increased or decreased by varying the temperature of the ambient environment in the environmental test chamber. The environmental test chamber can also be in communication with the meter electronics 20 and provide the temperature measurement of the meter electronics 20 to the meter electronics 20. Additionally or alternatively, the meter electronics 20 can obtain the temperature measurement from the temperature sensor 390 shown in FIG. 3.

In step 640, the method 600 can generate a signal parameter offset based on the measured temperature. For example, the method 600 could vibrate the flow tubes 130, 130' described in the foregoing and use the DSP output 362 to determine the signal parameter offset. In an embodiment, a nominal value of the phase difference between the pick-off sensors 310, 320 could be determined at a nominal temperature, such as room temperature, as corresponding to a zero flow rate. The temperature of the meter electronics 20 can be measured while vibrating the tube 130, 130' and cycling the temperature with the environmental test chamber. While cycling the temperature with the environmental test chamber, the phase difference can be measured.

The signal parameter offset can be generated by determining a difference between values determined as a nominal temperature and a value determined from the one or more signals obtained while cycling the temperature of the meter electronics 20. For example, the signal parameter offset can be determined by calculating the difference between the measured phase difference and the nominal temperature phase difference. Additionally or alternatively, the signal parameter offset can be determined by calculating the difference between a measured frequency and a nominal temperature frequency in, for example, a density measurement. Other signal parameters, such as amplitude, can be employed.

The signal parameter offset may also be correlated with the temperature measurements at different non-nominal temperatures by, for example, storing the signal parameter offset with the measured temperature in a database table. For example, the signal parameter offset 225 can be stored with the temperature measurement 224 in the storage system 220 in a single record in the database table. During operation, for example, the method 400 may read the appropriately selected signal parameter offset 225 and compensate the one or more signals with the signal parameter offset generated by method 600.

The generation of the signal parameter offset could be done as part of existing calibration routines or as a distinctly executed routine. For example, the vibratory meter 5 could be zeroed at room temperature to account for material properties in the flow tubes 130, 130', the effects of temperature on the tubes with the RTD 190, etc. Accordingly, the one or more signals may include a signal that is previously zeroed at the nominal temperature. Subsequently, the temperature of the meter electronics 20 could be measured while the ambient temperature around the meter electronics 20 is cycled as described in the foregoing. Accordingly, the temperature compensation can be determined after the vibratory meter 5 is zeroed to account for effects other than the temperature of the meter electronics 20.

In some embodiments, the signal parameter offset can be stored in, for example, the meter electronics 20. In the embodiment described with reference to FIG. 2, the signal parameter offset 225 can be stored in the storage system 220. The signal parameter offset 225 can be stored at about the same time as the correlated temperature measurement 224. For example, when the temperature of the meter electronics 20 is measured, the signal parameter offset 225 can be determined and then stored with the temperature measurement 224. In other embodiments, the signal parameter offset 225 can be generated for a range of temperature measurements with increments, such as ten ° C. increments. For example, a temperature measurement of 92° C. and a temperature measurement of 96° C. can be correlated with the same signal parameter offset 225.

The method 600 may be performed prior to the methods 400, 500. For example, the method 600 can be performed during manufacturing of the vibratory meter 5. Accordingly, the temperature measurement 224 and the signal parameter offset 225 can already be stored in the meter electronics 20 for use by the methods 400, 500 after vibratory meter 5 is installed at a customer site. The methods 400, 500 may use the stored temperature measurement 224 and the signal parameter offset 225 to compensate for temperature effects of the meter electronics 20 on a signal in the vibratory meter 5.

The embodiments described above provide an apparatus 300 and a method 400-600 for temperature compensation of a signal in a vibratory meter 5. As explained above, for example, the meter electronics 20 can cause one or more signals to vary due to temperature variations in the meter electronics 20. By compensating the one or more signals with a signal parameter offset, the variations in the one or more signals can be reduced or eliminated thereby yielding more accurate measurements over a range of temperatures.

As a result, the same vibratory meter 5 can, for example, be installed on an oil platform in an arctic climate and then later installed in a desert climate while reducing or eliminating the variations caused by the temperature variations in the meter electronics 20.

In some embodiments, the one or more signals can be used to determine a time delay between two of the pick-off sensors 170l, 170r, 310, 320. Temperature variations in the meter electronics 20 can therefore also cause the time delay to vary. As explained above, the time delay can be proportional to the difference between two of the one or more signals. These two signals may be conditioned by, for example, two different operational amplifiers 332 with discrete components. Therefore, variations in the values of the discrete components, such as the capacitors C, can cause variations in the time delay that are greater than the variations in the each of the one or more signals. Accordingly, adding the signal parameter offset to the time delay can also reduce or eliminate the variations in the time delay and the reduction may be greater than the reduction in the variations in each of the one or more signals.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other temperature compensations of a signal in a vibratory meter, and not just to the embodiments described above and shown in the accompanying figures. Accordingly, the scope of the embodiments described above should be determined from the following claims.

We claim:

1. A method for temperature compensation of a signal in a vibratory meter, the method comprising:
    obtaining one or more signals from a meter assembly in the vibratory meter;
    providing the one or more signals to an analog circuit of a meter electronics of the vibratory meter; and
    compensating the one or more signals with a signal parameter offset, wherein the signal parameter offset is based on a measured temperature of the analog circuit of the meter electronics.

2. The method of claim 1, wherein the step of obtaining the one or more signals from the meter assembly comprises obtaining one or more signals from at least one sensor attached to a tube in the meter assembly.

3. The method of claim 1, wherein the one or more signals includes a signal that is previously zeroed at a nominal temperature.

4. The method of claim 1, further comprising at least one of:
    determining a time delay between two of the one or more signals and compensating the time delay with the signal parameter offset;

determining a frequency of the one or more signals and compensating the frequency with the signal parameter offset; and determining an amplitude of the one or more signals and compensating the amplitude with the signal parameter offset.

5. The method of claim 1, further comprising measuring the temperature of the meter electronics and comparing the measured temperature with a stored measured temperature.

6. The method of claim 1, further comprising measuring the temperature of the meter electronics and correlating the measured temperature with the signal parameter offset.

7. The method of claim 1, wherein the one or more signals is comprised of at least one digital signal.

8. The method of claim 1, wherein the signal parameter offset is a digital value that is added to at least one of the one or more signals.

9. The method of claim 1, wherein the temperature of the analog circuit of the meter electronics is comprised of a temperature of a circuit board proximal to the analog circuit in the meter electronics.

10. A method for temperature compensation of a signal in a vibratory meter, the method comprising:
obtaining one or more signals from a meter assembly in the vibratory meter;
providing the one or more signals to an analog circuit of a meter electronics of the vibratory meter;
measuring a temperature of the analog circuit of the meter electronics;
generating a signal parameter offset based on the measured temperature; and
compensating the one or more signals with the signal parameter offset, wherein the signal parameter offset is based on the measured temperature of the analog circuit of the meter electronics.

11. The method of claim 10, wherein the step of generating the signal parameter offset based on the measured temperature comprises determining the difference between a nominal temperature value and a value determined from the one or more signals.

12. The method of claim 10, further comprising varying the temperature of the meter electronics by varying the temperature of the ambient environment.

13. The method of claim 10, further comprising storing the signal parameter offset and the temperature measurement in the meter electronics after the meter electronics have compensated the one or more signals with the signal parameter offset, the temperature measurement and the signal parameter offset used to determine another parameter offset with another temperature measurement.

14. The method of claim 10, further comprising storing a correlation between the temperature measurement and the signal parameter offset in the meter electronics.

15. An apparatus (300) for temperature compensation of a signal in a vibratory meter (5), the apparatus (300) comprising:
a meter assembly (10) in a vibratory meter (5), the meter assembly (10) being configured to provide one or more signals;
a meter electronics (20) communicatively coupled to the meter assembly (10), the meter electronics (20) comprising an analog circuit, the analog circuit being configured to receive the one or more signals from the meter assembly (10); and
a temperature sensor (390) in communication with the meter electronics (20), the temperature sensor (390) being configured to measure a temperature of the analog circuit of the meter electronics (20) and provide the temperature measurement (392) to the meter electronics (20);
wherein the meter electronics (20) is configured to:
provide a signal parameter offset based on the temperature measurement (392); and
compensate the one or more signals with the signal parameter offset.

16. The apparatus (300) of claim 15, wherein the meter assembly (10) is comprised of at least one flow tube (130, 130') and at least one pick-off sensor (170l, 170r, 310, 320) coupled to the at least one flow tube (130, 130').

17. The apparatus (300) of claim 15, wherein the meter electronics (20) is further configured to zero the one or more signals prior to compensating the one or more signals with the signal parameter offset.

18. The apparatus (300) of claim 15, wherein the meter electronics (20) is further configured to at least one of:
determine a time delay between two of the one or more signals and compensate the time delay with the signal parameter offset;
determine a frequency of the one or more signals and compensate the frequency with the signal parameter offset; and
determine an amplitude of the one or more signals and compensate the amplitude with the signal parameter offset.

19. The apparatus (300) of claim 15, wherein the meter electronics (20) provides the signal parameter offset by comparing the temperature measurement (392) to a stored temperature measurement (224) correlated with the stored signal parameter offset (225).

20. The apparatus (300) of claim 15, wherein the meter electronics (20) is further configured to store the temperature measurement (224) in a storage system (220) in the meter electronics (20).

* * * * *